(12) United States Patent
Pool et al.

(10) Patent No.: US 6,221,369 B1
(45) Date of Patent: Apr. 24, 2001

(54) HUMAN SKIN CARE PRODUCT AND METHOD

(76) Inventors: Dan B. Pool, 23 E. Surrey Rd., Phoenix, AZ (US) 85029; John T. Kreitzer, 8220 E. Montecito Ave., Scottsdale, AZ (US) 85251; David F. Kreitzer, 1601 E. Highland #1208, Phoenix, AZ (US) 85016

( * ) Notice: Subject to any disclaimer, the term of this patent is extended or adjusted under 35 U.S.C. 154(b) by 0 days.

(21) Appl. No.: 09/146,151

(22) Filed: Sep. 3, 1998

(51) Int. Cl.[7] .............................. A61K 6/00; A61K 7/00; A01N 25/34
(52) U.S. Cl. .............................. 424/401; 424/402
(58) Field of Search ................... 424/78.03, 402, 424/401

(56) References Cited

U.S. PATENT DOCUMENTS 5,780,047 * 7/1998 Kamiya et al. ...................... 424/443
5,968,533 * 10/1999 Porter et al. ......................... 424/401

* cited by examiner

Primary Examiner—Thurman K. Page
Assistant Examiner—S. Howard
(74) Attorney, Agent, or Firm—Parsons & Goltry; Robert A. Parsons; Michael W. Goltry

(57) ABSTRACT

A method of treating human skin including providing an impermeable patch having an adhesive on a side and a human skin treating composition containing an oxidizable element. A layer of the composition is applied to a portion of human skin and covered with the impermeable patch, whereby oxidation of the layer of the composition is retarded. The skin is smoothed of wrinkles prior to placement of the patch.

19 Claims, 1 Drawing Sheet

HUMAN SKIN CARE PRODUCT AND METHOD

FIELD OF THE INVENTION

This invention relates to human skin care.

More particularly, the present invention relates to a wrinkle removing method and apparatus.

BACKGROUND

Age, sun and many daily activities contribute to wrinkling and damage to skin particularly around the eyes and mouth. Thus, many people apply conditioning compositions in an attempt to eliminate these lines Currently, compositions containing vitamin C are believed to alleviate wrinkles. The vitamin C is carried by a patch which can be adhered to the skin. The problem with this approach is that the vitamin C is mixed into the adhesive on the patch, limiting the amount of vitamin C which can be applied to the area. Furthermore, vitamin C oxidizes in the presence of oxygen. Thus, the treated patches must be sealed in air tight envelopes. Also, the packaging is expensive because the patches have to be stored in foil wrappers to prevent deterioration of the vitamins by ultraviolet light. The envelope for a patch is opened prior to use. This is only partially effective, as the envelopes often contain air which, while small in volume will tend to oxidize the very small amount of vitamin contained on the patch.

Since most of these treatments are used at night during sleep, a strong adhesive must be used to prevent inadvertent removal of the patch. Also, since the vitamin is dried and mixed with the adhesive, to achieve greater amounts of vitamin C strong adhesives must be used. Oil must be used to dissolve the adhesive and remove the patch. This process can be very unpleasant.

Using the known products, the skin must be stretched manually with the fingers of one hand while placing the patch with the other hand. This process is cumbersome and the wrinkles which run parallel to the opposing forces of the fingers are not smoothed as well as wrinkles that run perpendicular to the stretching force. The smoother the wrinkles are when placing the patch the more effective the treatment.

It would be highly advantageous, therefore, to remedy the foregoing and other deficiencies inherent in the prior art.

Accordingly, it is an object of the present invention to provide a new and improved method of treating human skin.

Another object of the present invention is to provide a kit for treating wrinkles.

And another object of the present invention is to provide a method which keeps the composition effective by preventing oxidation and U.V. deterioration.

Still another object of the present invention is to provide a method of permitting the application of greater amounts of the composition.

Yet another object of the present invention is to provide a method and apparatus of treating skin which is easy to apply and remove after treatment.

SUMMARY OF THE INVENTION

Briefly, to achieve the desired objects of the instant invention, in accordance with a preferred embodiment thereof, provided is a method of treating human skin including providing an impermeable patch having an adhesive on a side and a human skin treating composition containing an oxidizable element. A layer of the composition is applied to a portion of human skin and covered with the impermeable patch, whereby oxidation of the layer of the composition is retarded. The skin is smoothed of wrinkles prior to placement of the patch. In a specific embodiment, the composition includes a smoothing ag ent which is allowed to dry prior to placement of the patch. In some embodiments, an adhesive may be employed which gradually deteriorates over a period of time, permitting the patch to be easily removed.

In accordance with a further embodiment of the invention, a skin conditioning kit is provided which includes a composition having an oxidizable element for topical application to wrinkled human skin. The composition is carried within an ultra-violet resistant sealable container for preventing oxidation and damage by ultra-violet light. Also provided is a patch of impermeable material with first and second opposed major surfaces having an adhesive on the first major surface for affixing the patch to the human skin. The adhesive on the first major surface is covered by a removable protective layer.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which.

DETAILED DESCRIPTION OF THE PREFERRED EMBODIMENTS

Figure 1:
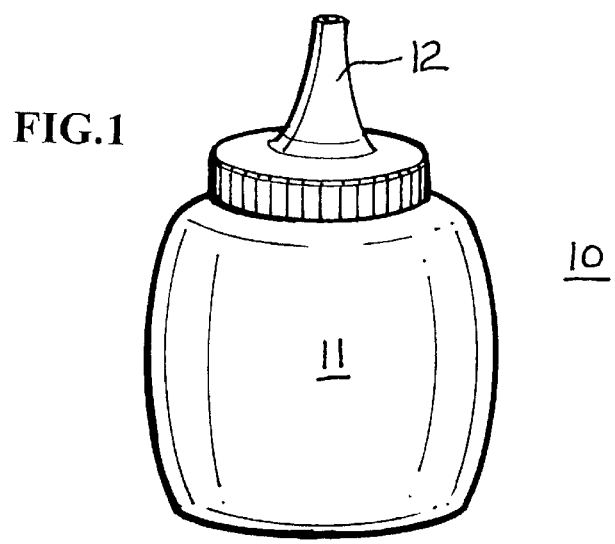
FIG. 1 is an isometric view of an ultra-violet resistant sealable container containing skin care composition.

Turning now to the drawings in which like reference characters indicate corresponding elements, attention is first directed to FIG. 1 which illustrates an ultra-violet resistant sealable container generally designated 10. Container 10 has a skin care composition 11 which includes an oxidizable element and a smoothing agent. Generally, the oxidizable element includes viable vitamins (e.g. vitamin C etc.) and nutrients along with natural protein toners which are known to provide the desired skin care. In addition to the oxidizable element, composition 11 includes a smoothing agent or toner which tightens the skin to smooth out wrinkles. Composition 11 is in a liquid or semi-liquid form which is easy to apply to desired portions or areas of the skin. The oxidizable element is kept fresh and in a natural form instead of being dried and placed in an adhesive on a patch. Therefore, the potency of the oxidizable element remains high.

In a preferred embodiment, container 10 is pliable and includes an applicator nozzle 12 so that as oxidizable element 11 is removed, e.g. by squeezing container 10, air does not enter to replace removed oxidizable material. Besides being sealable, to reduce the amount of air (oxygen) to which the oxidizable element is subjected, container 10 is constructed to include ultra-violet protection. To provide ultra-violet protection, container 10 can be formed of pliable opaque plastic materials which prevent ultraviolet light from entering or can be formed of a foil or other similar materials. The material of container 10 should also be selected so as to be inert relative to the oxidizable material so that no reactions between the oxidizable material and container 10 will take place.

Figure 2:
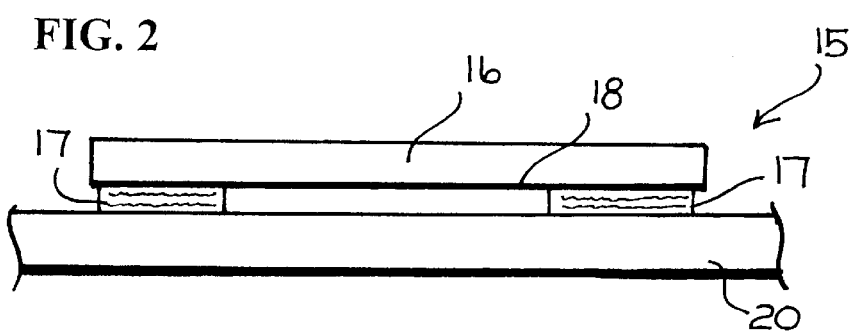
FIG. 2 is a sectional view of an impermeable patch according to the present invention.

Turning now to FIG. 2, a sectional view of an impermeable patch 15 is illustrated. Patch 15 includes a layer 16 of impermeable material, such as a soft flexible plastic or the like. Here it should be understood that layer 16 can include a plurality of sub-layers, one or more of which are impermeable material, if required, and all such embodiments are included within the definition of layer 16. An adhesive 17 is positioned on a major surface 18 of layer 16 and may either be distributed around the edges of surface 18 or may cover substantially the entire area of surface 18. Adhesive 17 is a material that gradually deteriorates over a period, generally 6 to 9 hours, after being applied to the skin. This gradual deterioration allows for easy removal of patch 15 when desired. During storage and before use, adhesive 17 on layer 16 is protected by a removable protective layer 20 positioned in contact with and covering major surface 18.

Figure 3:
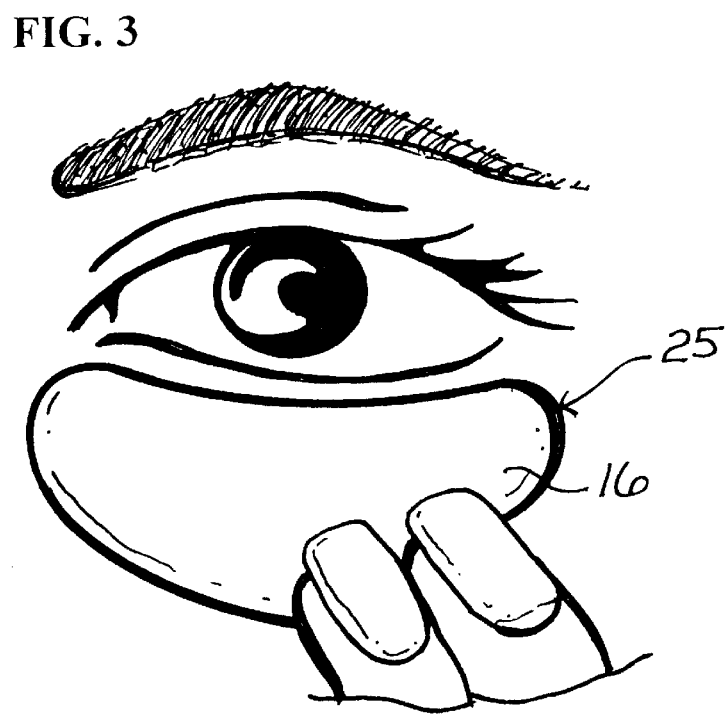
FIG. 3 is a partial perspective view of a patch of the present invention as it would appear in use.

In a preferred embodiment, container 10, which may be a tube or the like filled with composition 11, and a roll or sheets of patches 15 are supplied in a kit form. To use the kit, several drops, or the equivalent, are placed in the palm of the hand. Using a finger tip, composition 11 is transferred to a wrinkled area 25 (illustrated in FIG. 3) of the skin by gently patting composition 11 onto the surface of the wrinkled skin. The smoothing agent or toner in composition 11 is allowed to dry, which generally requires about 30 seconds. Protective layer 20 is pealed from a patch 15 and the exposed adhesive 17 is applied to area 25 in which composition 11 has been placed. Adhesive 17 is located around the periphery of layer 16 so that an airtight seal is formed, preventing ingress of air and preventing oxidation of the oxidizable element of composition 11. Air ingress is also prevented on patches with the adhesive covering the entire major surface.

Because patch 15 is generally applied before going to bed and allowed to remain through the night, upon awakening adhesive 17 will have deteriorated to a point that patch 15 can be easily and comfortably removed. Further, since composition 11 is stored in ultra-violet resistant sealable container 10 it is fresher and remains viable. Also, greater amounts can be placed on the wrinkled skin for better results. Because layer 16 of patch 15 is impermeable, the oxidizable element of composition 11 is shielded from the air and thereby kept from oxidizing.

Various modifications and changes to the embodiments herein chosen for purposes of illustration will readily occur to those skilled in the art. For example, container 10 can be formed in a variety of ways while still performing the stated functions. Other modifications and variations may be made by those skilled in the art without departing from the scope of the invention as defined by the following claims.

Having fully described and disclosed the present invention and preferred embodiments thereof in such clear and concise terms as to enable those skilled in the art to understand and practice same, the invention claimed is:

1. A method of treating human skin comprising the steps of:
   providing an impermeable patch having an adhesive on a side;
   providing a human skin treating composition containing an oxidizable element in a sealable container apart from the impermeable patch;
   applying a layer of the composition to a portion of human facial skin; and
   covering the layer of the composition and the portion of human skin with the impermeable patch, whereby oxidation of the layer of the composition is retarded.

2. A method as claimed in claim 1 wherein the adhesive on the side of the patch is adjacent edges of the patch.

3. A method as claimed in claim 1 wherein the adhesive on the side of the patch covers substantially all of the side of the patch.

4. A method as claimed in claim 1 wherein the portion of human skin includes wrinkles, and the step of covering the layer of the composition includes smoothing the skin prior to adhering the patch.

5. A method as claimed in claim 4 wherein the step of smoothing includes providing a smoothing agent in the composition.

6. A method as claimed in claim 4 wherein the step of smoothing includes manually smoothing the skin.

7. A method as claimed in claim 1 wherein the oxidizable element includes an oxidizable vitamin.

8. A method as claimed in claim 1, wherein the step of providing the impermeable patch includes providing the adhesive which deteriorates over a period of time.

9. A met hod of treating human skin comprising the steps of:
   providing a patch of impermeable material with first and second opposed major surfaces, the patch having an adhesive on the first major surface for affixing the patch to human skin;
   providing a container of human skin treating composition containing an oxidizable element and a skin smoothing agent, separate from the patch;
   applying a layer of the composition from the container to a wrinkled portion of an human skin;
   allowing the composition to substantially dry and smooth the portion of human skin; and
   covering the layer of the composition and the smoothed portion of human skin with the impermeable patch and affixing the patch to the portion of the human skin using the adhesive, whereby the layer of the composition on the portion of the human skin is protected from the ambient air and oxidation of the layer of the composition is retarded.

10. A method as claimed in claim 9 wherein the step of allowing includes allowing the composition to dry for approximately 30 seconds.

11. A method as claimed in claim 9 further including the step of leaving the patch on over approximately an eight hour period during which the adhesive deteriorates, permitting easy removal of the patch.

12. A method as claimed in claim 9 wherein the adhesive on the first major surface of the patch is adjacent edges of the patch.

13. A method as claimed in claim 9 wherein the adhesive on the first major surface of the patch covers substantially all of the first major surface of the patch.

14. A method as claimed in claim 9 wherein the oxidizable element include an oxidizable vitamin.

15. A skin conditioning kit comprising:
   a composition for topical application to wrinkled human skin, the composition containing an oxidizable element and carried within an ultra-violet resistant sealable container for preventing oxidation and damage by ultra-violet light; and
   a patch of impermeable material separate from the container, with first and second opposed major surfaces, the patch having an adhesive on the first major surface for affixing the patch to the human skin, the adhesive on the first major surface being covered by a removable protective layer.

16. A skin conditioning kit as claimed in claim 15 wherein the adhesive on the first major surface of the patch is adjacent edges of the patch.

17. A skin conditioning kit as claimed in claim 15 wherein the adhesive on the first major surface of the patch covers substantially all of the first major surface of the patch.

18. A skin conditioning kit as claimed in claim 15 wherein the composition includes a smoothing agent.

19. A skin conditioning kit as claimed in claim 15 wherein the oxidizable element includes an oxidizable vitamin.

\* \* \* \* \*